(12) United States Patent
Liu et al.

(10) Patent No.: US 10,556,970 B2
(45) Date of Patent: Feb. 11, 2020

(54) METHOD FOR PREPARING HIGH TRANSPARENT LOW ACYL GELLAN GUM

(71) Applicant: DSM IP ASSETS B.V., Te Heerlen (NL)

(72) Inventors: Guojun Liu, Shanghai (CN); Jie Zhao, Shanghai (CN); Chienkuo Yuan, Shanghai (CN)

(73) Assignee: DSM IP ASSETS B.V., Te Heerlen (NL)

( * ) Notice: Subject to any disclaimer, the term of this patent is extended or adjusted under 35 U.S.C. 154(b) by 0 days.

(21) Appl. No.: 15/946,058

(22) Filed: Apr. 5, 2018

(65) Prior Publication Data
US 2018/0291121 A1  Oct. 11, 2018

(30) Foreign Application Priority Data

Apr. 7, 2017  (CN) .......................... 2017 1 0227224

(51) Int. Cl.
| A23L 29/238 | (2016.01) |
| A61K 9/48 | (2006.01) |
| C08L 5/00 | (2006.01) |
| C08B 37/00 | (2006.01) |
| C12P 19/04 | (2006.01) |

(52) U.S. Cl.
CPC ........ *C08B 37/006* (2013.01); *C08B 37/0003* (2013.01); *C12P 19/04* (2013.01)

(58) Field of Classification Search
CPC . A61K 9/4816; C08L 5/00; C08L 5/14; A23L 29/238; A23L 29/244; A23L 29/25; A23L 19/115; A23V 2002/00
USPC ....................................................... 536/114
See application file for complete search history.

(56) References Cited

U.S. PATENT DOCUMENTS

| 6,660,172 | B2 * | 12/2003 | Koslow | ................. | A61L 2/0017 |
| | | | | | 210/777 |
| 8,231,921 | B2 | 7/2012 | Bezanson et al. | | |
| 2008/0145505 | A1 | 6/2008 | Bezanson et al. | | |
| 2011/0281307 | A1 * | 11/2011 | Yang | .................... | C08B 37/006 |
| | | | | | 435/101 |
| 2011/0281308 | A1 | 11/2011 | Wu et al. | | |

FOREIGN PATENT DOCUMENTS

| CN | 1351172 A | 5/2002 |
| CN | 1766120 A | 5/2006 |
| CN | 101824095 A | 9/2010 |
| CN | 102311508 A | 1/2012 |
| CN | 104193841 A | 12/2014 |
| EP | 2348054 A1 | 7/2011 |
| EP | 2436699 A1 | 4/2012 |

OTHER PUBLICATIONS

European Search Report, EP 18166331.1, dated Sep. 3, 2018.

* cited by examiner

*Primary Examiner* — Yih-Horng Shiao
(74) *Attorney, Agent, or Firm* — Maschoff Brennan; Brent A. Johnson; Yuefen Zhou

(57) ABSTRACT

A method for preparing high transparent low acyl gellan gum from fermentation broth is provided, in which two-stage filtrations are carried out on deacylated gellan gum fermentation broth by using diatomite and/or perlite with different particle sizes as filter aid and filter media. The obtained product has high gel transparency and low content of metal ions. The method also has the advantages of simple pretreatment of fermentation broth, high impurities removal efficiency, simple operation, and easy to be industrialized.

6 Claims, No Drawings

METHOD FOR PREPARING HIGH TRANSPARENT LOW ACYL GELLAN GUM

CROSS-REFERENCE TO RELATED APPLICATION

This application claims priority to the Chinese Patent Application No. 201710227224.X, filed Apr. 7, 2017, which is incorporated by reference by its entirety.

TECHNOLOGY FIELD

The present invention is related to the field of microbial hydrocolloids preparation. In particular, the present invention is related to preparation of purified low acyl gellan gum from gellan gum fermentation broth.

BACKGROUND

Microbial hydrocolloids are widely used in food industry, among which food-grade gellan gum is an important product. Gellan gum is usually in two forms: high acyl (HA) gellan gum and low acyl (LA) gellan gum. Low acyl gellan gum can be obtained by deacylation during the extraction of gellan gum fermentation broth. According to the transparency, low acyl gellan gum can be divided into two types: transparent type, and non-transparent type. The degree of transparency is related to the content of impurities contained in gellan gum. High transparent low acyl gellan gum can be obtained if the impurities are completely removed.

To the best of our knowledge, in known preparation techniques of low acyl gellan gum, fermentation broth must be pretreated and separated, and then water is added at high temperature to dissolve for deacylation. The disadvantages of current techniques are complicated operation, numerous steps, low product quality caused by easily hydrolysis of gellan gum during production, and high consumption of water and energy. In addition, one-step filtration is disclosed in the preparation of transparent low acyl gellan gum (such as CN101665778A), however, such filtration is not thorough enough and results in high content of impurities and low transmittance. Two-stage filtrations are also disclosed (such as CN1766120A, CN1351172A), where membrane is applied as filter media in second filtration. The disadvantage is that only small molecule gellan gum can pass through the small-size pores of membrane, while large molecule gellan gum is retained, resulting in low yield and less application value. To the best of our knowledge, there has been no report for preparing low acyl gellan gum by two-stage filtrations, wherein diatomite and/or perlite with different particle sizes is applied as filter media and filter aid.

The present invention provides a method for preparing high transparent low acyl gellan gum, including directly deacylation on fermentation broth, and carrying out two-stage filtrations, wherein diatomite and/or perlite with different permeabilities is used as filter media and filter aid.

DETAILED DESCRIPTION

The present invention provides a method for preparing purified low acyl gellan gum from gellan gum fermentation broth, including the following steps:
1) Deacylation of gellan gum fermentation broth, to obtain deacylated gellan gum solution;
2) First filtration of the deacylated gellan gum solution obtained in step 1), wherein filter aid and filter media used are diatomite and/or perlite with large particle size;
3) Second filtration of the gellan gum solution obtained in step 2), wherein filter aid and/or filter media used comprise diatomite and/or perlite with small particle size; and
4) Alcohol precipitation of the gellan gum solution obtained in step 3), drying, and milling to obtain the gellan gum product.

In the present invention, the deacylation in step 1) refers to removal of all or part of the acyl groups from high acyl gellan gum molecules in fermentation broth under heating and alkaline condition, to obtain low acyl gellan gum molecules.

As known by a skilled in the art, gellan gum fermentation yields the gum in its native high acyl form, and yields the gum in its low acyl form after deacylation. The deacylation may be carried out according to the methods disclosed in the art (such as CN103204949A, CN1932026A).

Generally, the deacylation in step 1) may be carried out as follows: heating gellan gum fermentation broth to 60-90° C., adjusting pH to alkaline condition, such as pH 9.0-11.0, preferably pH 10.0-10.5, stirring for 10-40 minutes, and then adjusting pH back to neutral, such as pH 4.0-8.0, preferably pH 6.0-7.0, to accomplish the deacylation.

In the present invention, the first filtration in step 2) may be carried out as follows: firstly, adjusting pH of the gellan gum solution obtained in step 1) to neutral, keeping for 10-60 minutes, preferably 10-30 minutes, more preferably 10-15 minutes, and then filtrating by using diatomite and/or perlite with large particle size as filter media and filter aid.

In the present invention, the diatomite and/or perlite with large particle size refers to diatomite and/or perlite with permeability of 1 $\mu m^2$-8 $\mu m^2$, preferably 2 $\mu m^2$-6 $\mu m^2$, more preferably 3 $\mu m^2$-5 $\mu m^2$.

In the present invention, the filter media is used for pre-coating on a filter to form pre-coated layer; the filter aid is used for adding into the gellan gum solution to be filtered, mixed, stirred, and then added into the pre-coated filter together with the solution.

In the first filtration, the added amount of the filter aid may be 10 g/L-60 g/L, preferably 10 g/L-50 g/L, more preferably 20 g/L-40 g/L based on the volume of the gellan gum solution to be filtered; the added amount of the filter media may be 10 g/L-60 g/L, preferably 10 g/L-50 g/L, more preferably 20 g/L-40 g/L based on the volume of the gellan gum solution to be filtered, such that the thickness of the pre-coated layer formed on the filter is 1.0 cm-4.0 cm, preferably 1.0 cm-3.0 cm, more preferably 2.0 cm-2.5 cm.

After the first filtration is carried out, most of the impurities are removed. The obtained gellan gum solution can be used for carrying out the second filtration in step 3).

In the second filtration, the filtration may be carried out by using filter aid and/or filter media comprising diatomite and/or perlite with small particle size. For example, the diatomite and/or perlite with large particle size used in step 2), and the diatomite and/or perlite with small particle size may be used as filter aid and/or filter media in the second filtration.

In the present invention, the diatomite and/or perlite with small particle size refers to diatomite and/or perlite with permeability of 0.1 $\mu m^2$-1.0 $\mu m^2$, preferably 0.2 $\mu m^2$-0.8 $\mu m^2$, more preferably 0.3 $\mu m^2$-0.5 $\mu m^2$.

In the second filtration, the added amount of the filter aid may be 10 g/L-60 g/L, preferably 10 g/L-50 g/L, more preferably 20 g/L-40 g/L based on the volume of the gellan gum solution to be filtered; the added amount of the filter media may be 10 g/L-60 g/L, preferably 10 g/L-50 g/L, more preferably 20 g/L-40 g/L based on the volume of the gellan gum solution to be filtered, such that the thickness of the pre-coated layer formed on the filter is 1.0 cm-4.0 cm, preferably 1.5 cm-3.0 cm, more preferably 2.0 cm-2.4 cm.

Preferably, in the second filtration, the filter aid used is the diatomite and/or perlite with small particle size, and the filter media used is the diatomite and/or perlite with large particle size and the diatomite and/or perlite with small particle size, wherein more preferably, the filter media is pre-coated layer by layer during pre-coating, such as: firstly, pre-coating the diatomite and/or perlite with large particle size, secondly, pre-coating the diatomite and/or perlite with small particle size. The added amount of the diatomite and/or perlite with large particle size in the first pre-coating may be 5 g/L-30 g/L, preferably 10 g/L-20 g/L, more preferably 10 g/L-15 g/L based on the volume of the gellan gum solution to be filtered, such that the thickness of the formed pre-coated layer on the filter is 0.7 cm-2.0 cm, preferably 0.8 cm-1.5 cm, more preferably 1.0 cm-1.2 cm; the added amount of the diatomite and/or perlite with small particle size in the second pre-coating can be 5 g/L-30 g/L, preferably 10 g/L-30 g/L, more preferably 10 g/L-15 g/L based on the volume of the gellan gum solution to be filtered, such that the thickness of the pre-coated layer formed on the first pre-coated layer on the filter is 0.7 cm-2.0 cm, preferably 0.8 cm-1.5 cm, more preferably 1.0 cm-1.2 cm.

In the present invention, the alcohol precipitation in step 4) may be carried out as follows: mixing the gellan gum solution obtained in step 3) with 1.0-5.0 volumes (preferably 1.5-3.0 volumes, more preferably 2.0-2.5 volumes) of ethanol or isopropyl with concentration of 60%-98% (v/v) (preferably 70%-95% (v/v), more preferably 85%-95% (v/v)) for precipitation, carrying out solid-liquid separation such as by centrifuge or screw extrusion press, drying, and milling to obtain the high transparent low acyl gellan gum product.

The present invention provides a method for preparing high transparent low acyl gellan gum product, including carrying out two-stage filtrations on deacylated fermentation broth of gellan gum, by using diatomite and/or perlite with different particle sizes as filter aid and filter media. The gellan gum product produced by the method of the present invention has transmittance higher than 85% after dissolution, preferably has transmittance of 85%-90%. The present invention also has the advantages of simple pretreatment of fermentation broth, high impurities removal efficiency, simple operation, and easy to be industrialized.

EXAMPLES

The present invention is further illustrated by the following examples. These examples are illustrative for the purpose of explaining the present invention, rather than limiting the scope of the present invention in any way.

Example 1

1) Heating and Deacylation of Gellan Gum Fermentation Broth

Firstly, 3 L gellan gum fermentation broth was heated to 90° C., and sodium hydroxide solution (10 wt %) was added to the broth to adjust pH to 10.0. After stirring for 15 minutes, then hydrochloric acid (10 wt %) was added to the system, to adjust pH back to 6.0, to obtain deacylated gellan gum solution.

2) First Filtration of Gellan Gum Solution 90 g diatomite with permeability of 4.0 $\mu m^2$ was used to form pre-coated layer with thickness of 2.0 cm in the filter, then 90 g diatomite with permeability of 4.0 $\mu m^2$ was added to the deacylated gellan gum solution obtained in step 1). After stirring and mixing for 40 minutes, the evenly mixed gellan gum solution was poured slowly into the pre-coated filter for first filtration, to obtain about 3.2 L gellan gum solution.

3) Second Filtration of Gellan Gum Solution 48 g diatomite with permeability of 3 $\mu m^2$ was added into the filter, to form the first pre-coated layer with thickness of 1.1 cm, then 48 g diatomite with permeability of 0.2 $\mu m^2$ was used to form the second pre-coated layer with thickness of 0.9 cm on the top of the first pre-coated layer. The total thickness of formed pre-coated layer is 2.0 cm.

90 g diatomite with permeability of 0.4 $\mu m^2$ was added to the gellan gum solution obtained from the first filtration. After stirring and mixing for 40 minutes, the evenly mixed gellan gum solution was poured into the pre-coated filter and filtration was carried out, to obtain about 3.0 L gellan gum solution.

4) Alcohol Precipitation of Gellan Gum Solution

The gellan gum solution obtained from the second filtration was stirred and cooled down to 60-65° C., then 2 volumes of 95% (v/v) ethanol was added and mixed while stirring for precipitation. Once the gellan gum fibers were completely precipitated out of the ethanol system, the fibers and ethanol mixture was separated with filter bag, to obtain squeeze dried gellan gum fiber materials with water content of 83%.

5) Drying and Sieving to Obtain Final Product

The squeeze dried fiber materials of low acyl gellan gum were put into drier for drying under 50° C. for 12 hours, then the water content of the fiber materials reached 8.6%. The yield of low acyl gellan gum was 1.0% (1 g low acyl gellan gum was recovered from per 100 ml fermentation broth). The dried fiber materials were milled and sieved by 60-mesh sieve, to obtain the gellan gum product.

Measurement of transmittance of the gellan gum product: (1) 0.3 g obtained gellan gum product was dispersed into 60 mL deionized water; (2) the obtained gellan gum solution was heated to boiling for 10 min on 420° C. graphite hotplate, while deionized water was supplemented to the system every 2 minutes during the heating, to keep a constant concentration of gellan gum within the system; (3) after heating, 1 mL calcium chloride solution (2.7%) was added under manually stirring; (4) the solution obtained after addition of calcium chloride was poured into 1 cm×1 cm glass cuvette, which was then covered and placed in the thermotank under 20° C. for 1 h to 2 h; (5) then the cuvette was placed in the spectrophotometer for transmittance measurement under 555 nm. The measured transmittance of the gellan gum product was 88%.

Example 2

1) Heating and Deacylation of Gellan Gum Fermentation Broth

Firstly, 3 L gellan gum fermentation broth was heated to 90° C., and sodium hydroxide solution (10 wt %) was added to the broth to adjust pH to 10.0. After stirring for 15 minutes, then hydrochloric acid (10 wt %) was added to the system, to adjust pH back to 6.0, to obtain deacylated gellan gum solution.

2) First Filtration of Gellan Gum Solution 92 g perlite with permeability of 4.5 $\mu m^2$ was used to form pre-coated layer with thickness of 2.1 cm in the filter, then 93 g perlite with permeability of 3.8 $\mu m^2$ was added to the deacylated gellan gum solution obtained in step 1). After stirring and mixing for 40 minutes, the evenly mixed gellan gum solution was poured slowly into the pre-coated filter for first filtration, to obtain about 3.3 L gellan gum solution.

3) Second Filtration of Gellan Gum Solution 50 g perlite with permeability of 4.5 µm² was added into the filter, to form the first pre-coated layer with thickness of 1.0 cm, then 50 g perlite with permeability of 0.4 µm² was used to form the second pre-coated layer with thickness of 1.0 cm on the top of the first pre-coated layer. The total thickness of formed pre-coated layer is 2.0 cm.

97 g perlite with permeability of 0.4 µm² was added to the gellan gum solution obtained from the first filtration. After stirring and mixing for 40 minutes, the evenly mixed gellan gum solution was poured into the pre-coated filter and filtration was carried out, to obtain about 3.1 L gellan gum solution.

4) Alcohol Precipitation of Gellan Gum Solution

The gellan gum solution obtained from the second filtration was stirred and cooled down to 60-65° C., then 2 volumes of 95% (v/v) ethanol was added and mixed while stirring for precipitation. Once the gellan gum fibers were completely precipitated out of the ethanol system, the fibers and ethanol mixture was separated with filter bag, to obtain squeeze dried gellan gum fiber materials with water content of 85%.

5) Drying and Sieving to Obtain Final Product

The squeeze dried fiber materials of low acyl gellan gum were put into drier for drying under 50° C. for 12 hours, then the water content in the fiber materials reached 7.8%. The yield of low acyl gellan gum was 1.1% (1.1 g low acyl gellan gum was recovered from per 100 mL fermentation broth). The dried fiber materials were milled and sieved by 60-mesh sieve, to obtain the gellan gum product. The measured transmittance was 89%, and the measurement was the same as that disclosed in Example 1.

Example 3

1) Heating and Deacylation of Gellan Gum Fermentation Broth

Firstly, 3 L gellan gum fermentation broth was heated to 90° C., and sodium hydroxide solution (10 wt %) was added to the broth to adjust pH to 10.0. After stirring for 15 minutes, then hydrochloric acid (10 wt %) was added to the system, to adjust pH back to 6.0, to obtain deacylated gellan gum solution.

2) First Filtration of Gellan Gum Solution 95 g diatomite with permeability of 3.0 µm² was used to form pre-coated layer with thickness of 2.2 cm in the filter, then 90 g perlite with permeability of 2.0 µm² was added to the deacylated gellan gum solution obtained in step 1). After stirring and mixing for 40 minutes, the evenly mixed gellan gum solution was poured slowly into the pre-coated filter for first filtration, to obtain 3.3 L gellan gum solution.

3) Second Filtration of Gellan Gum Solution 45 g perlite with permeability of 3.0 µm² was added into the filter, to form the first pre-coated layer with thickness of 1.2 cm, then 45 g diatomite with permeability of 0.5 µm² was used to form the second pre-coated layer with thickness of 1.0 cm on the top of the first pre-coated layer. The total thickness of formed pre-coated layer is 2.1 cm.

90 g diatomite with permeability of 0.5 µm² was added to the gellan gum solution obtained from the first filtration. After stirring and mixing for 40 minutes, the evenly mixed gellan gum solution was poured into the pre-coated filter and filtration was carried out, to obtain 3.1 L gellan gum solution.

4) Alcohol Precipitation of Gellan Gum Solution

The gellan gum solution obtained from the second filtration was stirred and cooled down to 60-65° C., then 2 volumes of 95% (v/v) ethanol was added and mixed while stirring for precipitation. Once the gellan gum fibers were completely precipitated out of the ethanol system, the fibers and ethanol mixture was separated with filter bag, to obtain squeeze dried gellan gum fiber materials with water content of 78%.

5) Drying and Sieving to Obtain Final Product

The squeeze dried fiber materials of low acyl gellan gum were put into drier for drying under 50° C. for 12 hours, then the water content in the fiber materials reached 7.6%. The yield of low acyl gellan gum was 1.2% (1.2 g low acyl gellan gum was recovered from per 100 mL fermentation broth). The dried fiber materials were milled and sieved by 60-mesh sieve, to obtain the gellan gum product. The measured transmittance was 87%, and the measurement was the same as that disclosed in Example 1.

The invention claimed is:

1. A method for preparing purified deacylated gellan gum from gellan gum fermentation broth, wherein the method comprises the following steps:
   1) Deacylation of gellan gum present in fermentation broth, to obtain deacylated gellan gum solution, followed by two-stage filtration consisting of steps 2) and 3);
   2) First filtration of the deacylated gellan gum solution obtained in step 1), wherein a first added filter aid and filter medium are diatomite and/or perlite with permeability of 1 µm²-8 µm²;
   3) Second filtration of the gellan gum solution obtained in step 2), wherein a second added filter aid or filter medium comprises diatomite and/or perlite with permeability of 0.1 µm²-1.0 µm²; and
   4) Alcohol precipitation of the gellan gum solution obtained in step 3), drying, and milling to obtain the gellan gum product.

2. The method according to claim 1, wherein in step 2), the added amount of said filter aid is 10 g/L-60 g/L based on the volume of the gellan gum solution to be filtered, and the added amount of said filter medium is 10 g/L-60 g/L based on the volume of the gellan gum solution to be filtered such that the thickness of the formed pre-coated layer is 1.0 cm-4.0 cm.

3. The method according to claim 1, wherein in step 3), the added amount of said filter aid is 10 g/L-60 g/L based on the volume of the gellan gum solution to be filtered, and the added amount of said filter medium is 10 g/L-60 g/L based on the volume of the gellan gum solution to be filtered such that the total thickness of the formed pre-coated layer is 1.0 cm-4.0 cm.

4. The method according to claim 1, wherein in step 3), said filter medium further comprises diatomite and/or perlite with permeability of 1 µm²-8 µm².

5. The method according to claim 4, wherein in step 3), said filter medium is pre-coated layer by layer.

6. The method according to claim 5, wherein in step 3), the diatomite and/or perlite with permeability of 1 µm²-8 µm² is used as filter medium to form first pre-coated layer on the surface of a filter, and the added amount of said filter medium is 5 g/L-30 g/L based on the volume of the gellan gum solution to be filtered such that the thickness of the formed first pre-coated layer is 0.7 cm-2.0 cm; and then the diatomite and/or perlite with permeability of 0.1 µm²-1.0 µm² is used as filter medium to form second pre-coated layer on the top of the first pre-coated layer, and the added amount of said filter medium is 5 g/L-30 g/L based on the volume of the gellan gum solution to be filtered such that the thickness of the formed second pre-coated layer is 0.7 cm-2.0 cm.

* * * * *